Figure 4:
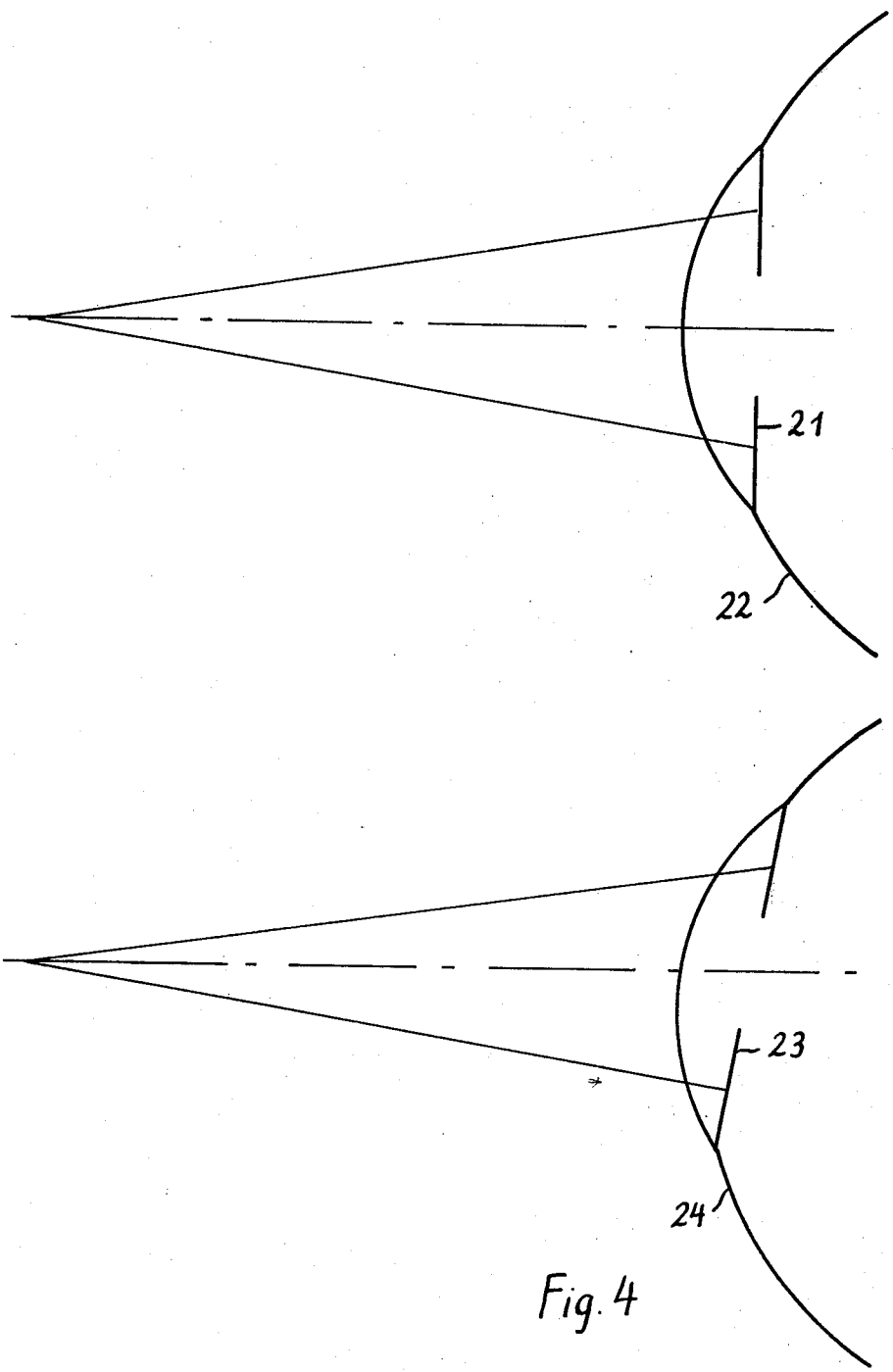

United States Patent [19]

Krumeich et al.

[11] 4,179,195

[45] Dec. 18, 1979

[54] METHOD AND APPARATUS FOR DETERMINING THE STRABISMUS ANGLE BETWEEN THE OPTICAL AXES OF A FIXING AND A STRABISMIC EYE

[75] Inventors: Jörg Krumeich, Wattenscheid; Hermann Rössler, Essen, both of Fed. Rep. of Germany

[73] Assignee: Hermann Rössler, Essen, Fed. Rep. of Germany

[21] Appl. No.: 787,063

[22] Filed: Apr. 13, 1977

[30] Foreign Application Priority Data

Apr. 15, 1976 [DE] Fed. Rep. of Germany ....... 2616870

[51] Int. Cl.² .............................................. A61B 3/08
[52] U.S. Cl. .......................................... 351/4; 351/5; 351/13; 351/39
[58] Field of Search .................... 351/39, 3, 2, 16, 13, 351/4, 5

[56] References Cited

FOREIGN PATENT DOCUMENTS 855799 12/1960 United Kingdom .......................... 351/2
885429 12/1961 United Kingdom .......................... 351/5

*Primary Examiner*—Paul A. Sacher
*Attorney, Agent, or Firm*—Martin A. Farber

[57] ABSTRACT

A method and apparatus for determining the strabismus angle between the optical axes of a fixing and of a strabismic eye, characterized in that from two light sources, the spacing of which from one another is adjusted to the pupillary distance of the fixing and of the strabismus eye respectively, one eye each is illuminated and a light reflection on the cornea of each eye is produced. By means of two optical receiving devices, the optical axes of which likewise are adjusted from one another to a distance corresponding to the pupillary distance of the eyes, the pupils of both eyes and both of the light reflections on the corneas of both eyes are imaged on one common image plane.

12 Claims, 6 Drawing Figures

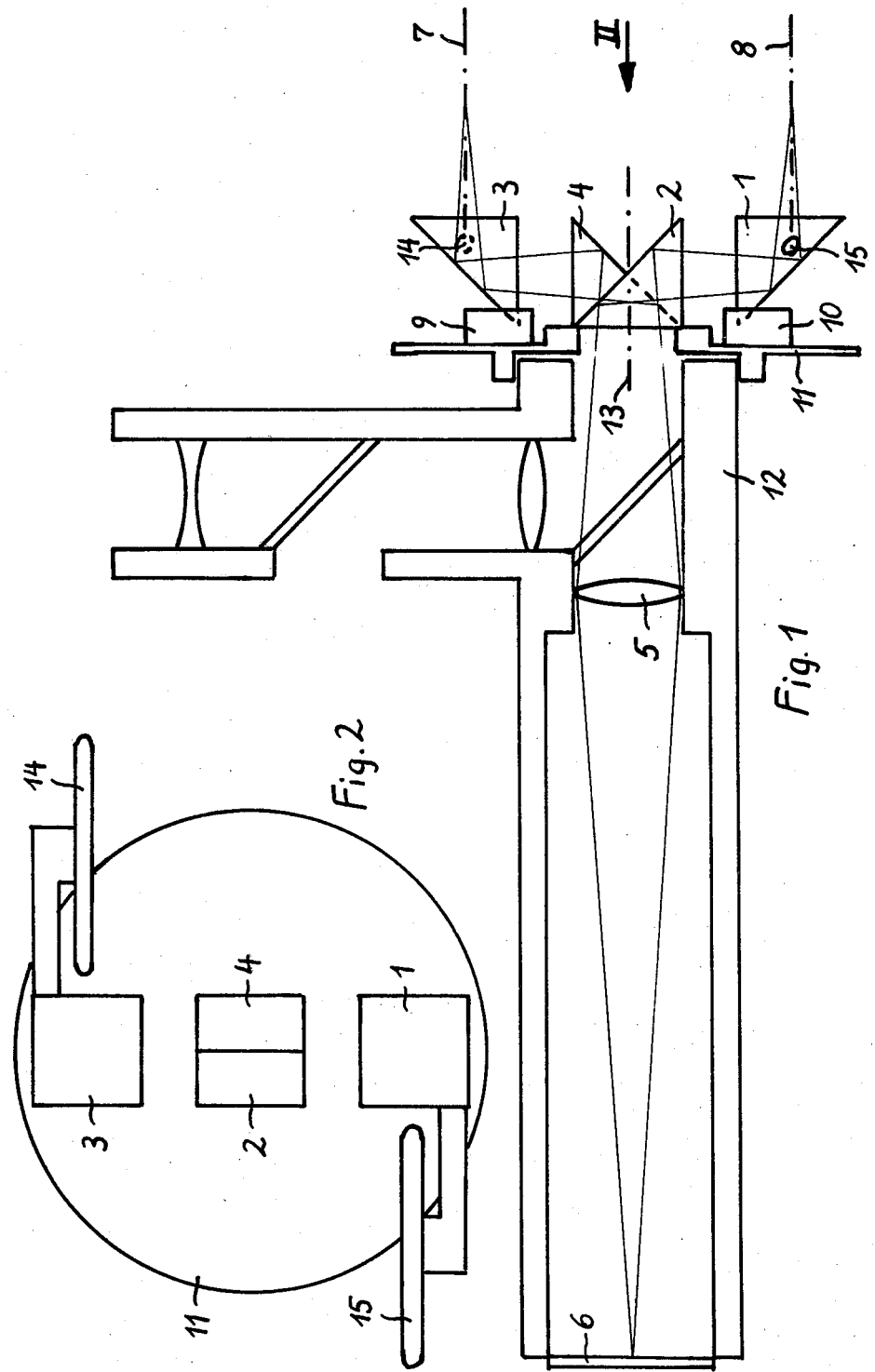

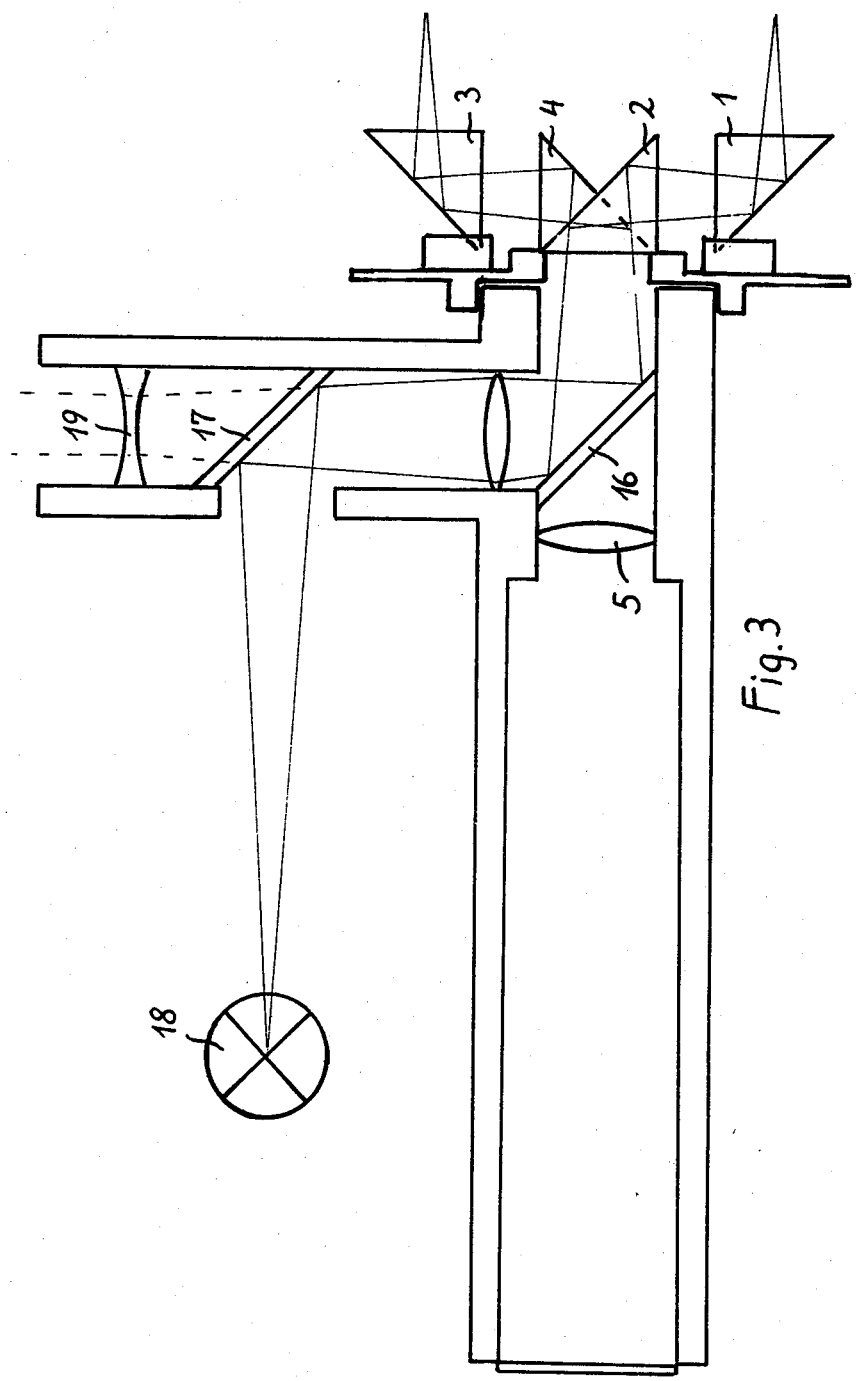

METHOD AND APPARATUS FOR DETERMINING THE STRABISMUS ANGLE BETWEEN THE OPTICAL AXES OF A FIXING AND A STRABISMIC EYE

The invention relates to a method for determining the strabismus angle between the optical axes of a fixing and of a strabismic eye as well as a device for performing this method.

Strabismus is an eye disorder. Strabismus means that the optical axes of both eyes, which optical axes are designated also as the center point axes, are not directed on the same object. Strabismus has the consequence that either a weak-sightedness or amblyopia of the strabismic eye arises as a consequence of non-use or that none or a false cooperation of both eyes is produced or built up in the visual center. It is thus necessary to avoid, operatively or with the aid of glasses, the strabismus position as early as possible, i.e., thus already with small children. As a condition for the extent or measurement of the eye muscle displacement or for the correction with the help of prisms, the strabismic angle must be determined.

One known method for measurement of the strabismus angle resides in that prisms are added in front of the strabismic eye as long as the eyes are alternatingly covered until the strabismus position is neutralized or equalized by the deflection of a specific prism, of which the deflection angle of this prism provides the strabismus angle. With another known method the strabismus angle is measured with the help of the so-called Maddox-cross. In this manner the normal, fixing eye is guided or directed along a scale until the light reflection of a lamp which is projected from the intersection point of the cross is imaged with the other eye centrally on the cornea. From the then scale marking seen from the fixing eye, the strabismus angle can be calculated or can be directly read off with a corresponding scale gauge or calibration. A further known measuring method takes place with the help of a device built according to the principle of the so-called haploscope. In this manner the right eye and the left eye each present the image by means of two separated optical viewing systems, which with strabismic sight at first is seen as two images lying next to one another. By horizontal pivoting of the two optical viewing systems with respect to one another, as a rule the two images for the strabismus can be associated or positioned together into a common or joint image impression, from which the pivot angle of the optical viewing system provides the strabismus angle. All previously mentioned methods have the disadvantage that the measuring of the strabismus angle is not sufficiently precise. With the prism methods and with the Maddox-cross, it is not possible to exactly determine the strabismus angle with babies or small children, since the children do not calmly or quietly fix and both of these methods presume a calm fixing or staring. The methods with a device built according to the principle of the haploscope are not usuable with infants or small children, since the subjective statements concerning the image impression which are necessary for these methods cannot be expected from children. First of all the known measuring methods have the disadvantage that they supply no documentary data, particularly no photographic recording, with which it would be possible, at any time to control and exactly compare the original condition before a removal of the strabismus angle and the condition after treatment with one another, in order in this manner to make possible and to documentarily record evidence or demonstration of the progress and of the result of the treatment.

The invention has set the task to develop a method and an apparatus for determining the strabismus angle, which avoids the disadvantages of the known methods and devices and which provides an exact and moreover documentary recordable measuring result for determining the strabismus angle.

The method found for solution of this task touches on the recognition that the reflection produced on the cornea of the eyes by a light source illuminating the eyes lies on the cornea of the strabismus eye at a different position than on the cornea of the normal eye, and in the first place resides in that from two light sources the spacing of which from one another is adjusted to the pupillary distance of the fixing and of the strabismus eye respectively, one eye each is illuminated and a light reflection on its cornea is produced and that by two optical receiving devices, the optical axes of which likewise are adjusted from one another to a distance corresponding to the pupillary distance, the pupils of both eyes and both of the light reflections on the corneas of both eyes are imaged on one common image plane. From the position of the light reflection in the image of the normal eye with respect to its imaged pupil, it is able to be determined at which nominal-position the light reflection in the image of the strabismus eye must lie, if it were not strabismic, and the distance between this nominal-position and the actual position of the light reflection in the image of the strabismus eye serves as a measure of the strabismic angle, which angle can be measured or can be registered as the longitudinal measure of this distance or also can be calculated over the trigonometric functions in angular degrees. The imaging of both of the eyes and of the light reflections produced on their corneas for example can be made directly visible on the image plane; in a particularly advantageous manner with the method in accordance with the invention, the image can be photographed for the analysis and evaluation and measuring or calculation, respectively, of the strabismus angle, by means of projecting the image on a negative or film material as the image plane.

Essential and important is that the two light sources producing the light reflections as well as the two optical receiving or recording devices which produce the image on the image plane are adjusted to the pupillary distance of the two eyes, by which the spacing between the center points of the pupil of the normal eye and of the pupil of the strabismic eye is indicated. For this purpose an advantageous further formation of the method in accordance with the present invention resides in, that by means of one auxiliary light source through both of the optical receiving devices, both eyes are lit up and directed with light, and an image of the auxiliary light source is produced on the iris of both eyes respectively, and that both of the optical receiving devices are adjusted or shifted in the plane disposed through the optical axes of both receiving devices by such an amount, and/or this plane is so rotated or inclined about an axis of symmetry extending parallel to both of the optical axes by such an amount, until with both eyes a sharp image of the auxiliary light source lies on the same position of the irises. For example, by means of the optical receiving or pick-up devices, circular images from the correspondingly formed auxiliary light source, the center point of each of which circular image lying in the optical axis of the respective receiving devices, can be projected through the corneas of the eyes, on their irises, so that quickly and accurately by means of cross-adjustment of the receiving devices in the plane passing through their optical axes, an adjustment or setting of the spacing of the receiving devices to the pupillary distance is achieved when both of the circular images of the auxiliary light source lie on the iris of the two eyes. By means of inclination of the plane in which the two receiving devices lie with their optical axes, the position of the receiving devices furthermore can be adjusted about the parallel-extending axis of symmetry to a possible inclined holding of the head. If the auxiliary light source, e.g. is arranged at the same optical distance away from the receiving devices as the image plane, the production of a sharp image of the auxiliary light source on the iris of both eyes by adjustment of the receiving devices in the direction of their optical axes simultaneously serves as a measure for the focusing of the receiving devices, in order to obtain sharp images on the image plane during the imaging of the eye pupils and of the light reflections.

The formation of the inventive device resides in the first place in that the apparatus has two optical receiving devices for imaging respectively one eye each by one receiving device on a common image plane, the receiving devices being aligned axially parallel with their optical axes, and each optical receiving device is coordinated to a light source for illuminating the eyes and that the two optical receiving devices as well as the two light sources are displaceably guided transversely to the direction of the optical axes of the receiving devices for changing their spacing relative to each other corresponding to the pupillary distance of the eyes. The light sources, which serve for the production of the light reflection on the corneas of the two eyes, can be formed from two distance-variable light exits or outlets of a single lamp, advantageously they comprise two lamps separated form one another, preferably flashlights. In further execution of the apparatus, on the side of the receiving devices facing the image plane there is arranged an auxiliary light source, which enables light to be emitted passing through the receiving devices in the direction of their optical axes for the production of an image of the auxiliary light source on the eye respectively coordinated to each receiving device. This auxiliary light source can also comprise two separated lamps or two light outlets or exits of a single lamp. A particularly expedient advantageous formation of the apparatus in accordance with the invention resides in that the two optical receiving devices are made of two optical deflection devices, whose optical axes which are directed on the eyes to be imaged are distance-adjustable, and a common optical image portion for both deflection devices which is arranged between the deflection devices and the image plane. With this apparatus both of the eyes, i.e., the pupil and iris and the light reflection of both eyes which is produced on the cornea, can be imaged superimposed on the image plane, i.e., brought into congruence. This is of particular advantage in order to be able to photographically record the images by means of a single camera, the objective of which camera then forms the common optical image part for both of the receiving devices. This facilitates and simplifies the respective determination of the measurement of the strabismus angle, and since the film format of the camera is available for the single image which is brought into congruence, the imaging and photographic recording can take place in increased scale or measure for the additional raising of the measuring precision. The two optical deflection systems can be made of mirrors or preferably of prisms. Moreover the two optical deflection devices can be formed in an advantageous manner such that one deflection device projects the upper half of one eye which is to be imaged and the other deflection device projects the lower half of the other eye which is to be imaged across the common optical image part onto the common image plane.

Additional features of the device in accordance with the invention result from the following description and the drawing, which shows one embodiment example of the inventive apparatus and is explained according to the also inventive method.

In the drawing show

Figure 5:
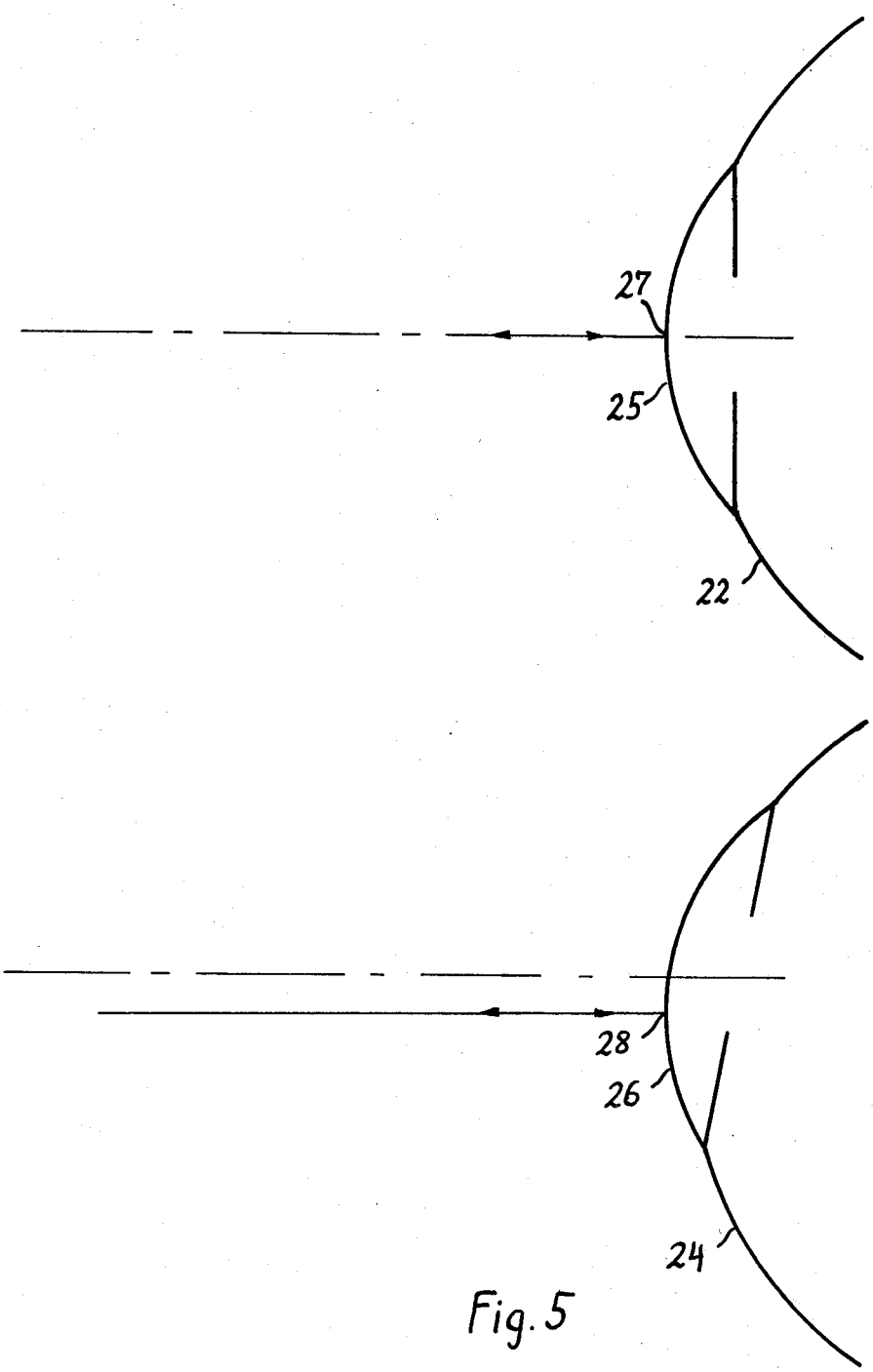
Figure 6:
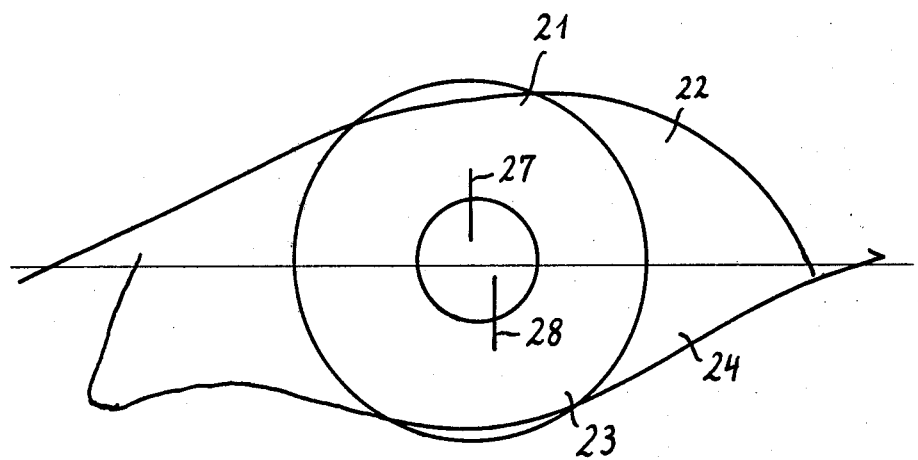

FIG. 1 a plan view of the apparatus in schematic illustration, whereby in this Fig. the course of the light rays is indicated with the image of the eyes and the light reflection;

FIG. 2 a view of the apparatus in the direction of the arrow II in FIG. 1;

FIG. 3 a view of the apparatus corresponding to FIG. 1, whereby in this Fig. the course of the light rays is indicated during the adjustment and alignment of the apparatus to the pupillary distance of the eyes;

FIG. 4 a schematic illustration of a normal and a strabmisic eye during the adjustment operation of the apparatus;

FIG. 5 an illustration of both eyes during the imaging- and measuring-operation, respectively, corresponding to FIG. 4;

FIG. 6 a schematic illustration of the image of the eyes produced by the apparatus.

The apparatus possesses a first optical deflection device comprising prisms 1 and 2 and a second optical deflecting device comprising prisms 3 and 4. Furthermore the apparatus has an optical image or projection portion 5, formed for example by a camera objective, in common for the two deflection devices, on the side of the image portion 5 which faces away from the deflection devices there being arranged an image plane 6. As indicated in FIG. 1 the prism 1 turns or directs the light rays falling on one of the deflection devices toward the associated prism 2 which deflects the light rays into the image portion 5. Analogously the light falling in the prism 3 of the other deflection device is deflected into the associated prism 4 and from the latter likewise into the image portion 5. The two deflection devices together with the common image constitute two optical receiving or pick-up devices which produce the image at the same position on the image plane 6. In order to be able to adjust the spacing of the optical axes 7 and 8 of both of the deflection devices to the pupillary distance of both eyes, the prisms 1 and 3 are displacably mounted in the plane passing through the optical axes 7 and 8 by means of holders 9 and 10 on a plate 11. The plate 11 is rotatably mounted on the housing 12 so that the plane which passes through the optical axes 7 and 8 can be inclined about the axis of symmetry 13, in this manner in order to be able to adjust the two deflection devices also to a possibly inclined position of the eyes.

The prisms 2 and 4 have, as may be recognized from FIG. 2, only half the height of the respectively coordinated prisms 1 and 3, so that as will still be described, from the deflection device comprising the prisms 1 and 2, only for example the upper half of that eye is imaged or projected across the image portion 5 on which eye this deflection device is aligned with its optical axis 8, and by the deflection device comprising the prisms 3 and 4 only for example the lower half of that eye is imaged over the image portion 5 on which eye this deflection device is aligned with its optical axis 7.

Each deflection device is coordinated to a light source 14 and 15, respectively. These light sources 14 and 15 are formed advantageously line-like, and for example can comprise straight light or flashlight tubes. These line-like light sources 14 and 15 are arranged such that their longitudinal direction intersects the optical axes 7 and 8, respectively, of the associated deflection device, and indeed in a preferred manner, perpendicularly to the plane passing through the optical axes 7 and 8. By this manner of arrangement of the light sources 14 and 15, the result is that also the spacing of the two light sources 14 and 15 from each other is adjusted to the eye pupillary distance when the spacing of the optical axes 7 and 8 of the two deflection devices is adjusted to the pupillary distance. Corresponding to the arrangement of the prisms 2 and 4 with respect to each other and their coordination to the prisms 1 and 3, the light sources 14 and 15 are arranged on opposite sides of the prisms 1 and 3 as this may be recognized in FIG. 2.

An imaging device is arranged between the optical deflection devices and the optical image portion 5, which imaging device contains two plane mirrors 16 and 17 (FIG. 3). An auxiliary lighting source 18 is arranged spaced from this imaging device. The plane mirror 16—when it is not a folding or hinged mirror but rather a stationary mirror,—is a semi-permeable plane mirror, so that the light rays falling into the deflection devices partially are able to pass through the mirror 16 into the image portion 5. On the other side the light of the auxiliary light source 18 can be reflected into the two deflection devices via the mirrors 16 and 17, from the prisms 1 and 3 thereof the light being reflected in the direction of the optical axes 7 and 8 toward the eyes. The imaging device additionally is constructed as an observation or viewing device with the aid of a lens 19 so that by the imaging and via the two prisms—deflection devices, the eyes, which are illuminated with the light of the auxiliary light source 18, can also be observed.

For adjustment of the spacing of the optical axes 7 and 8 of the two deflection devices, as well as in cooperation consequently of the distance between the two light sources 14 and 15, to the pupillary distance, both of the eyes are illuminated with the auxiliary light source 18 (see FIG. 3) and produce, as FIG. 4 illustrates, on the iris 21 of a normal, fixing eye 22 and on the iris of a strabismic eye 24, respectively, a sharp image each of the auxiliary light source 18. The prisms 1 and 3, together with the light sources 14 and 15, are shifted on the plate 11 such that the image of the auxiliary light source 18 is centrally located on the iris 21 and 23, respectively, of both of the eyes. Then the distance of the optical axes 7 and 8 and the distance of the light sources 14 and 15 corresponds to the pupillary distance of both of the eyes 22 and 24. This adjustment can be directly controlled via the lens 19 of the imaging- and observation-device.

After the adjustment of the apparatus takes place, with the aid of the light sources 14 and 15, respectively, a light reflection is produced on the cornea 25 of the eye 22 (FIG. 5) and on the cornea 26 of the eye 24, and simultaneously from both eyes and the produced light reflection, images are produced on the image plane 6 with the aid of the prisms-deflection devices (FIG. 1). In this manner on the basis of the described construction and arrangement of the prisms 2 and 4, the upper half is imaged for example of the eye 22, and the lower half of the eye 24, as this is evident from FIG. 6, whereby both of the image halves are united such that they complement or complete one another to form the image of one iris and one pupil.

With an exactly fixing normal eye 22, the light on the cornea 25 is reflected at the position 27 which lies in the optical axis. With the strabismic eye 24 to the contrary, the light is not reflected in the optical axis from the cornea 26 into the deflection device aligned on this eye, but rather the light reflection appears at the position 28 which does not lie in the optical axis. As a consequence of this, on the produced divided image of both eyes (FIG. 6) there appears a light reflection 27 on the fixing eye 22 and a light reflection 28 on the strabismic eye 24, which reflections are offset or displaced with respect to each other. The strabismus angle is able to be determined and calculated from the spacing of the two imaged light reflections 27 and 28. The image plane 6 can directly be the film of a camera so that the image illustrated in FIG. 3 can be recorded as photographs.

We claim:

1. A method for determining the strabismus angle between the optical axes of a fixing and of a strabismic eye, comprising the steps of adjusting the spacing of the centers of two light sources from one another to the pupillary distance of the fixing and of the strabismus eye respectively, adjusting the spacing of parallel optical axes of two optical receiving devices from one another with the optical axes remaining parallel to one another to a distance corresponding to the pupillary distance, illuminating each eye from said two light sources, respectively, and producing a light reflection on the corneas of the eyes, and imaging the pupils of both eyes and both of the light reflections on the corneas of both eyes on one common image plane via the two optical receiving devices.

2. The method according to claim 1, wherein the steps of adjusting the spacing of the optical axes of the two optical receiving devices and of the centers of the two light sources is performed by the steps of positioning the light sources with a distance between their centers corresponding to the distance between the optical axes of the two optical receiving devices, directing light from one auxiliary light source through both of the optical receiving devices onto both eyes, and producing a sharp image of the auxiliary light source on the iris of both eyes respectively, and displacing both of the optical receiving devices together with the two light sources in a plane disposed through the optical axes of both receiving devices by such an amount, until the sharp image of the auxiliary light source lies on the same position of the irises of both eyes.

3. The method according to claim 1, wherein the steps of adjusting the spacing of the optical axes of the two optical receiving devices and of the centers of the two light sources is performed by the steps of directing light from one auxiliary light source through both of the optical receiving devices onto both eyes, and producing a sharp image of the auxiliary light source on the iris of both eyes respectively, positioning the light sources with a distance between their centers corresponding to the distance between the optical axes of the two optical receiving devices, displacing both of the optical receiving devices together with the two light sources in a plane disposed through the optical axes of both receiving devices by such an amount, and rotating this plane about an axis of symmetry extending parallel to both of the optical axes by such an amount, until the sharp image of the auxiliary light source lies on the same position of the irises with both eyes.

4. The method according to claim 1, wherein the steps of adjusting the spacing of the optical axes of the two optical receiving devices and of the centers of the two light sources is performed by the steps of positioning the light sources with a distance between their centers corresponding to the distance between the optical axes of the two optical receiving devices, directing light from one auxiliary light source through both of the optical receiving devices onto both eyes, and producing a sharp image of the auxiliary light source on the iris of both eyes respectively, tilting both of the optical receiving devices together with the two light sources by the rotation of an imaginary plane disposed through the optical axes of both receiving devices about an axis of symmetry thereof extending parallel to both of the optical axes by such an amount until the sharp image of the auxiliary light source lies on the same position of the irises with both eyes.

5. An apparatus for determining the strabismus angle between the optical axes of a fixing eye and a strabismic eye, comprising a common image plane, two optical receiving means for imaging respectively one eye each by one of said receiving means onto said common image plane, said receiving means each defining an optical axis and being aligned axially parallel with said optical axes, two light source means, each for respectively illuminating one of the eyes, are coordinated to said two optical receiving means, respectively, and said two optical receiving means and said two light source means are mounted transversely displaceable to the direction of the optical axes of said receiving means for changing the respective spacing of the centers of the two light source means as well as the spacing of the optical axes of said two optical receiving means relative to one other corresponding to the pupillary distance of the eyes.

6. The apparatus according to claim 5, further comprising an auxiliary light source arranged on a side of said optical receiving means which faces said common image plane and operatively positioned so as to enable light to radiate through said optical receiving means in the direction of the optical axes of the latter to produce an image of said auxiliary light source on each eye respectively coordinated to each of said optical receiving means.

7. The apparatus according to claim 5, wherein said two light source means are formed line-like and each of said two light source means intersects the optical axis of one of said optical receiving means coordinated thereto.

8. The apparatus according to claim 7, wherein each of said two light source means intersects the optical axis of said one of said optical receiving means perpendicularly to a plane disposed through the optical axes of both of said optical receiving means.

9. The apparatus according to claim 5, wherein said two optical receiving means comprise two optical deflection devices having said optical axes thereof respectively directed on the eyes to be imaged, said optical deflection devices and said optical axes thereof are spacing-adjustable, and a common optical image part for both said two optical deflection devices arranged between said two optical deflection devices and said common image plane.

10. The apparatus according to claim 9, wherein said two optical deflection devices are formed such that one of said deflection devices enables a projection of the upper half of one eye to be imaged and the other of said deflection devices enables a projection of the lower half of the other eye to be imaged, both projections across said common optical image part onto said common image plane.

11. The apparatus according to claim 9, further comprising reflecting means arranged between said optical deflection devices and said optical image part, said reflecting means is light permeable for transmission of light rays from said optical deflection devices across said common optical image part to said common image plane, and a single auxiliary light source in common for both of said deflection devices, said auxiliary light source is arranged laterally from said common image plane, and said auxiliary light source is operatively arranged such that light therefrom is able to reflect into both of said deflection devices to radiate against the respective eyes.

12. The apparatus according to claim 11, wherein said reflecting means includes an observation device formed in the direction of reflecting of the light of the auxiliary light source.

* * * * *